United States Patent
Clausen et al.

(10) Patent No.: US 10,098,521 B2
(45) Date of Patent: *Oct. 16, 2018

(54) VISUALISING A 3D DENTAL RESTORATION ON A 2D IMAGE

(71) Applicant: 3Shape A/S, Copenhagen K (DK)

(72) Inventors: Tais Clausen, Klagshamn (SE); Rune Fisker, Virum (DK)

(73) Assignee: 3SHAPE A/S, Copenhagen K (DK)

(*) Notice: Subject to any disclaimer, the term of this patent is extended or adjusted under 35 U.S.C. 154(b) by 0 days.

This patent is subject to a terminal disclaimer.

(21) Appl. No.: 15/690,471

(22) Filed: Aug. 30, 2017

(65) Prior Publication Data

US 2018/0049620 A1 Feb. 22, 2018

Related U.S. Application Data

(63) Continuation of application No. 14/773,564, filed as application No. PCT/EP2014/054495 on Mar. 7, 2014, now Pat. No. 9,775,491.

(30) Foreign Application Priority Data

Mar. 8, 2013 (DK) .................................. 2013 00125

(51) Int. Cl.
*A61B 1/00* (2006.01)
*A61B 1/24* (2006.01)
(Continued)

(52) U.S. Cl.
CPC ........ *A61B 1/00009* (2013.01); *A61B 1/0005* (2013.01); *A61B 1/24* (2013.01); *A61C 13/0004* (2013.01); *A61C 13/34* (2013.01)

(58) Field of Classification Search
CPC ..... A61C 1/084; A61C 8/0089; A61C 9/0046; A61C 7/002; A61C 13/0022;
(Continued)

(56) References Cited

U.S. PATENT DOCUMENTS 6,914,599 B1 7/2005 Rowe et al.
7,110,594 B2 9/2006 Jones et al.
(Continued)

FOREIGN PATENT DOCUMENTS

DE 10 2004 052683 A1 5/2006
EP 1 444 965 A2 8/2004
(Continued)

OTHER PUBLICATIONS

International Search Report (PCT/ISA/210) dated May 22, 2014, by the European Patent Office as the International Searching Authority for International Application No. PCT/EP2014/054495.
(Continued)

*Primary Examiner* — Haixia Du
(74) *Attorney, Agent, or Firm* — Buchanan Ingersoll & Rooney PC

(57) ABSTRACT

A method for visualising a 3D dental restoration on a 2D image of the mouth of a patient includes obtaining a 3D dental model of at least a part of the patient's oral cavity, designing the 3D dental restoration, obtaining the 2D image of the mouth of the patient, estimating a virtual camera including at least one virtual camera property corresponding to at least one physical camera property of the physical camera used to obtain the 2D image, viewing the 3D dental restoration using the virtual camera, determining the visible area of the 3D dental restoration, which is not overlapped by surrounding anatomic features when viewed with the virtual camera, imaging the visible area of the 3D dental restoration with the 2D image. This advantageously provides an image which with high accuracy gives the dentist and the patient a visual presentation of the final result of a dental treatment.

18 Claims, 2 Drawing Sheets

(51) Int. Cl.
*A61C 13/34* (2006.01)
*A61C 13/00* (2006.01)

(58) Field of Classification Search
CPC ..... A61C 8/0036; A61C 19/05; A61B 5/4547; G06T 1/0007; G06T 17/00; G06T 2207/30036
See application file for complete search history.

(56) References Cited

U.S. PATENT DOCUMENTS

| 8,092,215 B2 | 1/2012 | Stone-Collonge et al. |
| 2004/0219490 A1 | 11/2004 | Gartner et al. |
| 2009/0316966 A1 | 12/2009 | Marshall et al. |

FOREIGN PATENT DOCUMENTS

| WO | WO 2008/128700 A1 | 10/2008 |
| WO | WO 2012/000511 A1 | 1/2012 |
| WO | WO 2012/006717 A1 | 1/2012 |
| WO | WO 2009/141248 A1 | 9/2014 |

OTHER PUBLICATIONS

Written Opinion (PCT/ISA/237) dated May 22, 2014, by the European Patent Office as the International Searching Authority for International Application No. PCT/EP2014/054495.

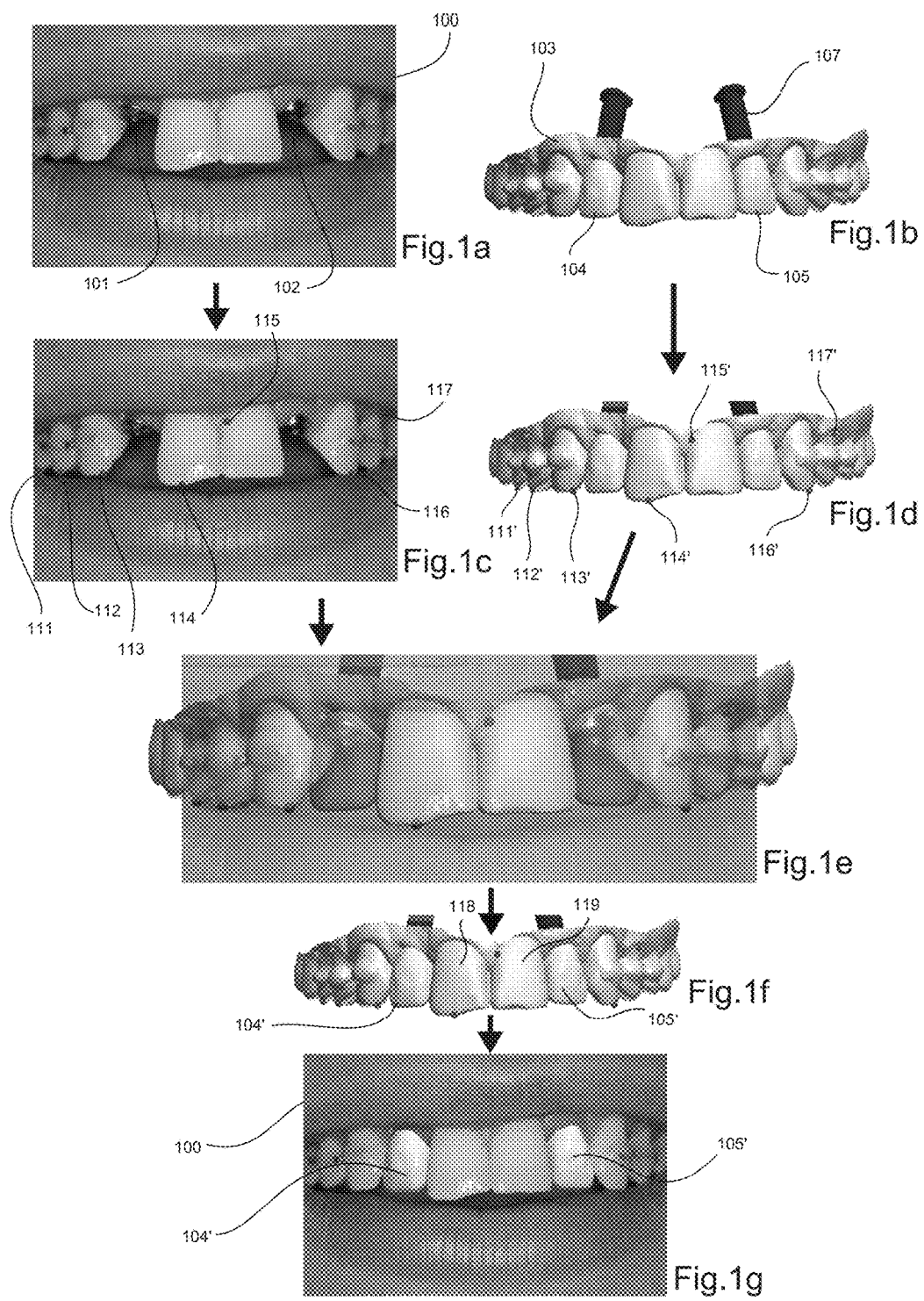

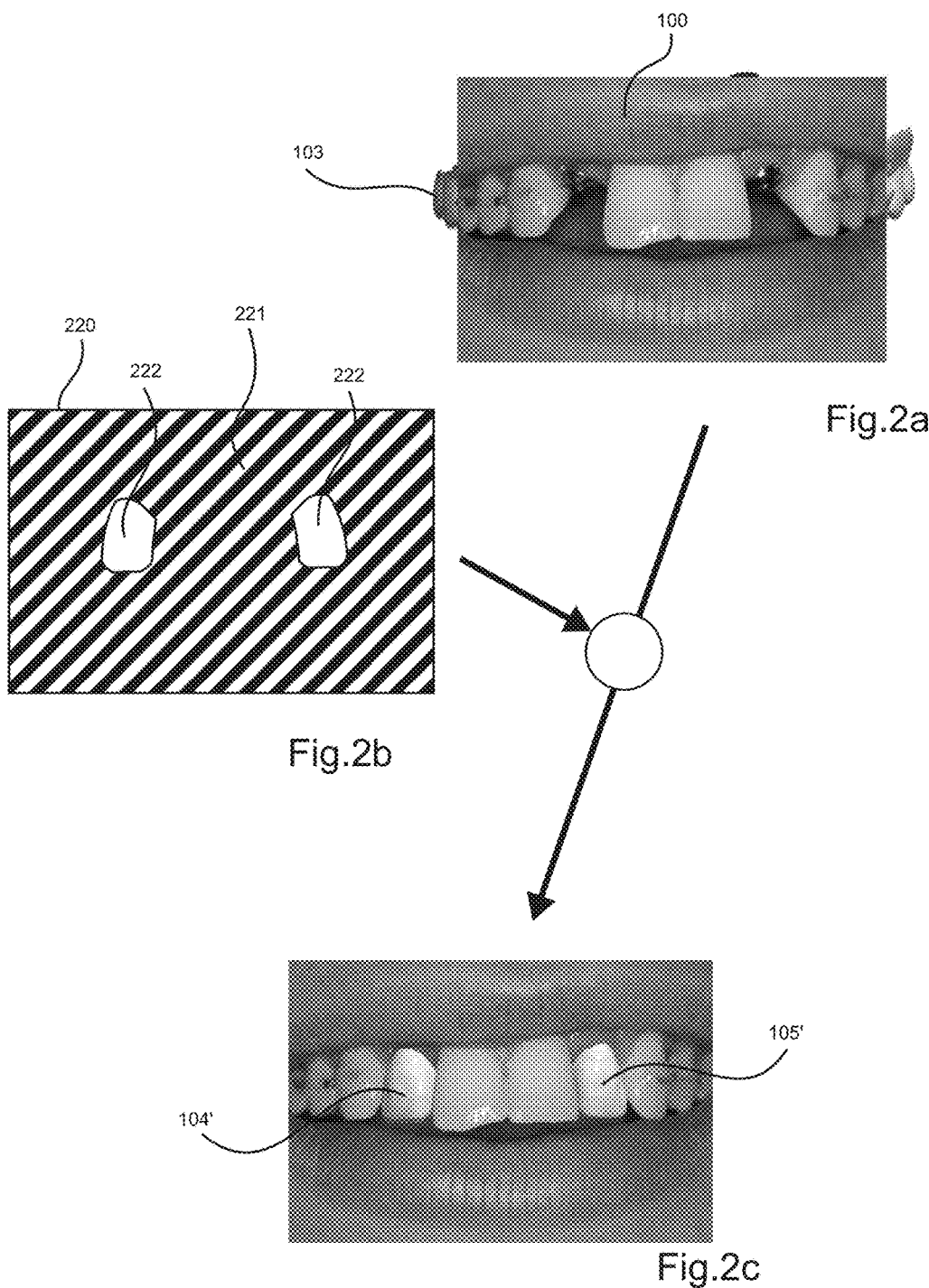

VISUALISING A 3D DENTAL RESTORATION ON A 2D IMAGE

CROSS-REFERENCE TO RELATED APPLICATIONS

The present application is a continuation of U.S. patent application Ser. No. 14/773,564, which was filed in the U.S. on Sep. 8, 2015, and which is a national stage of PCT International Application No. PCT/EP2014/054495, filed Mar. 7, 2014, which claims priority of Danish Patent Application No. PA 2013 00125, filed Mar. 8, 2013. The subject matter of U.S. patent application Ser. No. 14/773,564; PCT International Application No. PCT/EP2014/054495; and Danish Patent Application No. PA 2013 00125 are incorporated herein by reference.

FIELD OF THE INVENTION

The disclosure relates to a method for visualising a 3D dental restoration on a 2D image of a mouth. In particular the method relates to a method where overlapping surrounding anatomic features, such as gingiva, teeth and lip, are considered when visualising the 3D dental restoration.

BACKGROUND

When planning dental treatment it can often be difficult to project the final result. The lab technician and dentist typical have an idea, but it can be difficult to convey this to the patient.

Today it is becoming common to design a large part of restoration using CAD/CAM software. By using the digital files produced during design of restoration it has become possible to visually show the expected result when the restoration has been finally placed in the oral cavity.

SUMMARY

The present disclosure relates to a method for visualising a 3D dental restoration on a 2D image of the mouth of a patient, wherein the method comprises:
  obtaining a 3D dental model of at least a part of the patient's oral cavity,
  designing the 3D dental restoration,
  obtaining the 2D image of the mouth of the patient,
  estimating a virtual camera comprising at least one virtual camera property corresponding to at least one physical camera property of the physical camera used to obtain the 2D image,
  viewing the 3D dental restoration using the virtual camera,
  determining the visible area of the 3D dental restoration, which is not overlapped by surrounding anatomic features when viewed with the virtual camera,
  imaging the visible area of the 3D dental restoration with the 2D image.

This advantageously provides an image which with high accuracy gives the dentist and the patient a visual presentation of the final result of a dental treatment.

It should of course be understood that more than one 3D dental restoration may be visualised on the 2D image at one time.

Obtaining the 3D dental model can for example be done by scanning, either using an intra-oral scanner or a desktop scanner where a dental impression or a gypsum model is scanned. The obtained scan may then directly be processed as a 3D dental model or the scan may be further processed, e.g. cleaned up, before it is used as a 3D dental model.

The 3D dental restoration is typically designed based on the 3D dental model. This allows the dental technician to take into account features such as neighboring and antagonist teeth and gingiva profiles.

The 2D image may be a digital photo taken of the patient when naturally smiling. The photo may be taken using any standard digital camera. Imaging the visible area of the 3D dental restoration can be done by projecting the visible pixels of the restoration onto the 2D image.

In one embodiment the visible area of the 3D dental restoration is determined with the 3D dental restoration placed in the 3D dental model. This allows for neighboring and antagonist teeth to be taken into account when determining the visible area.

Typically the 3D dental restoration is designed based on a 3D dental model which shows surrounding anatomic features such as adjacent gum surfaces and neighboring and antagonist teeth. Using the 3D dental model to identify overlapping areas of the surrounding anatomic features provides a very accurate determination of the visible area of the 3D dental restoration and thus a very esthetically visualised final image.

The virtual camera is determined by estimating at least one physical camera property of the physical camera which was used to obtain the 2D image. One such camera property can for example be the field of view (FOV), which is dependent on the focal length (f) of the lens used and the sensor size (ss) of the camera. For a normal lens the field of view can be calculated accordingly:

$$FOV=2\times\arctan(ss/2f).$$

In one embodiment the virtual camera is estimated by
  marking at least a first, second, third and fourth reference point on the 2D image and corresponding at least first, second, third and fourth reference point on the 3D dental model,
  aligning the at least first second, third and fourth reference point with the respective corresponding at least first second, third and fourth reference point.

As discussed above, in order to determine/estimate the transformation, i.e. rotation, position and scale of the model; and the physical camera property, e.g. the focal length and/or the field of view with which the model is viewed at least four reference points needs to be marked. Accordingly, by providing at least four reference points a unique model and very precise model can be determined for the virtual camera. Adding more reference points will even further increase the accuracy of the model, however, the accuracy also depends on how exact the reference points are placed.

The principles for determining the virtual camera are for example described in "Marker-Free Human Motion Capture: Estimation Concepts and Possibilities with Computer Vision Techniques from a Single Camera View Point" by Daniel Grest, published by LAP LAMBERT Academic Publishing (Jul. 22, 2010), ISBM-13:978-3838382227.

In another embodiment the visible area of the 3D dental restoration is determined by identifying overlapping anatomic features in the 2D image of the mouth and subtracting the overlapping anatomic features from the 3D dental restoration.

The surrounding anatomic feature is typically the gingiva, a posterior tooth and/or the lip.

Anatomic features such as the gingiva and/or neighboring teeth can be determined by segmenting the 3D dental model. By evaluating the 3D dental model when seen with the virtual camera it is possible to determine how these anatomical features overlap the 3D dental restoration.

Other anatomical features which are not present in the 3D dental model may be manually identified. For example, in some situations the anatomical feature us the lip which in some cases will cover some of the visible area of the 3D dental restoration. Accordingly, in one embodiment in order to inform the system that the lip overlaps the dental restoration the method further comprises defining the edge of the lip in the 2D image.

In one embodiment the at least one physical camera property is the field of view (FOV). The field of view provides the basic information for properly viewing a virtual model from the same point of view and perspective as was it done at the same spot in the physical environment. Accordingly, by estimating the field of view of the physical camera the virtual view becomes highly realistic.

In one embodiment the visible area of the 3D dental restoration is imaged with the 2D image by projecting the visible are of the 3D dental restoration onto the 2D image.

In another embodiment the visible area of the 3D dental restoration is imaged with the 2D image by generating a mask aligned with the 2D image, said mask having a first value in the areas of the 2D image overlapping the 3D dental restorations and a second value in the areas where no overlap occur.

Advantageously the 2D image can be set to be transparent in the areas where the mask has the first value.

Use of masks and masking techniques are well known in the art and by knowing how to use them in general as described above the person skilled in the art will know how to apply the appropriate techniques.

In one the method further comprises adjusting the transparency of the 2D image. This allows the user to switch between viewing the 3D dental restorations alone and in some embodiment change the design thereof and viewing the 3D dental restorations with the 2D image to evaluate the expected result.

In one aspect there is further disclosed a computer user interface for visualising a 3D dental restoration on a 2D image of the mouth of a patient, wherein the computer user interface comprises:
   a tool for loading a 2D image of the mouth of a patient,
   a tool for providing a 3D dental model of at least a part of the patient's oral cavity,
   a tool for providing a 3D dental restoration,
   a tool for estimating a virtual camera comprising at least one virtual camera property corresponding to at least one physical camera property of the physical camera used to obtain the 2D image,
   a view area for imaging the visible area of the 3D dental restoration, which is not overlapped by surrounding anatomic features when viewed with the virtual camera, with the 2D image.

In one embodiment the tool for estimating the virtual camera comprises
   marking at least a first, second, third and fourth reference point on the 2D image and corresponding at least first, second, third and fourth reference point on the 3D dental model.

In another embodiment the user interface further comprises a tool for adjusting the transparency of the 2D image. This can for example be in the shape of a slider wherein the level of transparency is adjusted.

In yet another embodiment the interface further comprises a tool for defining the edge of the lip in the 2D image. This can for example be done by drawing a closed curve around the edge of the lips all around the opening of the mouth.

In one aspect the disclosure relates to a method for estimating a physical camera used to obtain a 2D image of the mouth of a patient, wherein the method comprises:
   obtain a 3D dental model ,
   obtain a 2D image of the mouth of the patient,
   mark at least a first, second and third reference point on the 2D image and corresponding at least first, second and third reference point on the 3D dental model,
   align the at least first second and third reference point with the respective corresponding at least first second and third reference point.

FIGURES

FIG. 1a- 1g illustrates a method for visualising a 3D dental restoration on a 2D image of the mouth of a patient as discussed herein.

FIG. 2a-2c illustrates another embodiment of a method for visualising a 3D dental restoration on a 2D image of the mouth of a patient as discussed herein.

DETAILED DESCRIPTION

A method for visualizing a 3D dental restoration 1, 2 on a 2D image of the mouth of a patient 3 is described with respect to FIG. 1.

A 2D image 100 of the mouth of a patient as shown in FIG. 1a is obtained. The image can for example be obtained by using a standard digital camera. The patient is asked to smile as he or she normally would in order to obtain the image in a natural position. Anatomical features, such as lips, gingiva and surrounding teeth, are thereby placed in their normal position relative to the dental restorations and the end result is easier evaluated.

In many cases the 2D image shows the entire face as this gives a better impression of the total expected result.

The current case shown in FIG. 1 is an implant case where the two upper incisors (FDI index 12 and 22) have been extracted and implants have been placed. The healing abutments 101, 102 can be seen in the 2D image. A 3D dental model 103 of the upper jaw is shown in FIG. 1b. The 3D dental model is obtained by 3D scanning, for example using an intra-oral scanner which scans directly in the mouth of the patient. In other embodiment the 3D model may be obtained from a desktop scanner which scans an impression taken of the teeth in the mouth or a gypsum model made from the impression.

3D dental restorations 104, 105 of the missing incisors have been virtually designed and placed in the 3D dental model. Implant analogs 106, 107 virtually shows the placement of the implants and have been used as basis for designing the 3D dental restorations.

With the 3D dental restorations 104,105, the 3D model 103 and the 2D image 100 obtained the physical camera used to take the 2D image is estimated so that the 3D model and the 3D dental restorations may be viewed from the same camera view, i.e. from a virtual camera which corresponds to the physical camera.

In the current embodiment described in FIG. 1 the physical camera is estimated by marking seven reference points 111, 112, 113, 114, 115, 116 and 117 in the 2D image. The corresponding reference points 111', 112', 113', 114', 115', 116' and 117' are also marked on the 3D model 103. In the current case this is done manually for high accuracy. Although seven reference points are used a lower or higher number could be used. Typically a lower number will decrease the accuracy, however, the accuracy is also determined on how precise the reference points are placed and thus, four reference points could also be used with the same accuracy.

With the reference points placed the virtual camera can be estimated and the 3D model and 3D restoration can be aligned with the 2D image and the field of view (FOV) of physical camera used to obtain the 2D image can be estimated as described in "Marker-Free Human Motion Capture: Estimation Concepts and Possibilities with Computer Vision Techniques from a Single Camera View Point" by Daniel Grest, published by LAP LAMBERT Academic Publishing (Jul. 22, 2010), ISBM-13:978-3838382227.

The virtual camera is then used to view the 3D dental restorations and the 3D model from the same field of view. Subsequently the 3D model and 3D restoration are aligned with the 2D image by aligning the respective reference points to each other. The alignment involves a transformation such as shifting the position rotating and scaling the 3D model so that the reference points align correctly. When the alignment has been applied to the 3D model, the 3D restoration can be overlaid very precisely on top of the 2D image as shown in FIG. 1e.

Moreover, with the correct camera view on the 3D model and the 3D restorations the visible areas 104', 105' of the 3D restorations can be determined.

In this way overlapping surrounding anatomic features, such as the front incisors 118, 119 (FDI index 11 and 21), can be taken into consideration as will be understood.

The visible areas 104', 105' of the dental restorations can then be projected onto the 2D image of the mouth of the patient. The final image gives the dentist and patient a highly accurate view of how the outcome of the dental treatment will look like.

For even better esthetics the 3D restoration could be rendered in the 3D model.

In another embodiment as mask 220 is generated in order to image the visible areas 104', 105' of the dental restorations.

FIG. 2a corresponds to FIG. 1e wherein the 3D model 103 with the 3D dental restorations are viewed with the virtual camera having the same field of view as the camera used to take the 2D image 100, and the 3D model with the 3D dental restoration aligned to the 2D image.

As can be seen the 2D image is in front of the 3D model with the 3D dental restorations. Accordingly, in order to image the visible areas of 3D dental restorations with the 2D image the mask 220 is generated.

The mask has a size which corresponds to the 2D image and the visible areas of the 3D dental restorations are defined in the mask. Accordingly, the area of the mask not identifying the visible area of the 3D dental restorations 221 have one value, e.g. black, and the area identifying the visible area of the 3D dental restorations 222 have another value, e.g. white. The mask then function as a template where all white areas overlapping the 2D image renders that area of the 2D image transparent and the black areas renders that areas of the 2D image opaque. Accordingly, the 3D dental restorations can be seen through the 2D image. The above generally describes the principles of using masks, and as such masking techniques are commonly used in the art and the person skilled in the art will be able to apply them based on the above. Such masking techniques are for example commonly used with graphics editing programs such as Photoshop developed by Adobe Systems.

The invention claimed is:

1. A method for visualising a 3D dental restoration on a 2D image of a mouth of a patient, wherein the method comprises:
    obtaining a 3D dental model of at least a part of the patient's oral cavity,
    designing the 3D dental restoration in the 3D dental model,
    obtaining the 2D image of the mouth of the patient,
    selecting only a visible portion of the 3D dental restoration, and
    imaging only the selected visible portion of the 3D dental restoration with the 2D image, wherein the 2D image is not visible at the selected visible portion of the 3D dental restoration.

2. A method according to claim 1, wherein the method further comprises:
    determining the visible portion of the 3D dental restoration.

3. A method according to claim 2, further comprising:
    marking at least a first, second, third and fourth reference point on the 2D image and corresponding to at least first, second, third and fourth reference points on the 3D dental model,
    aligning the at least first, second, third and fourth reference points with the respective corresponding at least first second, third and fourth reference points on the 3D dental model.

4. A method according to claim 1, wherein the visible portion of the 3D dental restoration is determined by identifying overlapping anatomic features in the 2D image of the mouth and subtracting the overlapping anatomic features from the 3D dental restoration.

5. A method according to claim 4, wherein the surrounding anatomic feature is a gingiva, a posterior tooth and/or a lip.

6. A method according to claim 5, wherein the method further comprises defining an edge of the lip in the 2D image.

7. A method according to claim 1, further comprising estimating a virtual camera comprising at least one virtual camera property corresponding to at least one physical camera property of a physical camera used to obtain the 2D image, wherein the at least one physical camera property is the field of view.

8. A method according to claim 1, wherein the visible portion of the 3D dental restoration is imaged with the 2D image by projecting the visible portion of the 3D dental restoration onto the 2D image.

9. A method according to claim 1, wherein the visible portion of the 3D dental restoration is imaged with the 2D image by generating a mask aligned with the 2D image, said mask having a first value in areas of the 2D image overlapping the 3D dental restoration and a second value in areas where no overlap occur.

10. A method according to claim 9, wherein the 2D image is transparent in the areas where the mask has the first value.

11. A method according to claim 1, wherein the method further comprises adjusting a transparency of the 2D image.

12. A system for visualising a 3D dental restoration on a 2D image of a mouth of a patient, wherein the system enables:
    loading a 2D image of the mouth of the patient,
    providing a 3D dental model of at least a part of the patient's oral cavity,
    providing a 3D dental restoration in the 3D dental model, selecting only a visible portion of the 3D dental restoration, and imaging only the selected visible portion of the 3D dental restoration with the 2D image, wherein the 2D image is not visible at the selected portion of the 3D dental restoration.

13. A system according to claim 12, wherein the system further enables marking at least a first, second, third and fourth reference point on the 2D image and corresponding to at least first, second, third and fourth reference points on the 3D dental model.

14. A system according to claim 12, wherein the system further enables adjusting a transparency of the 2D image.

15. A system according to claim 12, wherein the system further enables defining an edge of a lip in the 2D image.

16. A system according to claim 12, wherein the visible portion of the 3D dental restoration is determined by identifying overlapping anatomic features in the 2D image of the mouth and subtracting the overlapping anatomic features from the 3D dental restoration.

17. A method according to claim 16, wherein the surrounding anatomic feature is a gingiva, a posterior tooth and/or a lip.

18. A system for visualising a 3D dental restoration on a 2D image of a mouth of a patient, wherein the system comprises a hardware processor configured to:
 load a 2D image of the mouth of the patient,
 provide a 3D dental model of at least a part of the patient's oral cavity,
 provide a 3D dental restoration in the 3D dental model,
 select only a visible portion of the 3D dental restoration, and
 image only the selected visible portion of the 3D dental restoration with the 2D image, wherein the 2D image is not visible at the selected portion of the 3D dental restoration.

* * * * *